(12) United States Patent
Chapin, Jr. et al.

(10) Patent No.: US 12,049,364 B2
(45) Date of Patent: Jul. 30, 2024

(54) ROUTING OF TOTES AND BOTTLES WITHIN A PHARMACY CONVEYOR SYSTEM

(71) Applicant: Innovation Associates, Inc., Johnson City, NY (US)

(72) Inventors: Fletcher A. Chapin, Jr., Maine, NY (US); Todd Bower, Johnson City, NY (US)

(73) Assignee: Innovation Associates, Inc., Johnson City, NY (US)

(*) Notice: Subject to any disclaimer, the term of this patent is extended or adjusted under 35 U.S.C. 154(b) by 209 days.

(21) Appl. No.: 17/698,484

(22) Filed: Mar. 18, 2022

(65) Prior Publication Data
US 2022/0306399 A1 Sep. 29, 2022

Related U.S. Application Data

(60) Provisional application No. 63/164,831, filed on Mar. 23, 2021.

(51) Int. Cl.
| | |
|---|---|
| *B65G 43/08* | (2006.01) |
| *B65G 43/10* | (2006.01) |
| *B65G 47/53* | (2006.01) |
| *B65G 47/82* | (2006.01) |
| *G16H 20/10* | (2018.01) |
| *B65G 47/50* | (2006.01) |

(52) U.S. Cl.
CPC .............. *B65G 43/08* (2013.01); *B65G 43/10* (2013.01); *B65G 47/53* (2013.01); *B65G 47/82* (2013.01); *G16H 20/10* (2018.01); *B65G 47/503* (2013.01); *B65G 2201/0244* (2013.01); *B65G 2201/0258* (2013.01); *B65G 2201/027* (2013.01); *B65G 2203/0216* (2013.01)

(58) Field of Classification Search
CPC ........ B65G 43/08; B65G 43/10; B65G 47/53; B65G 47/82; B65G 47/503; B65G 2201/0244; B65G 2201/0258; B65G 2201/027; B65G 2203/0216; G16H 20/10
USPC .......................................... 198/444
See application file for complete search history.

(56) References Cited

U.S. PATENT DOCUMENTS

| | | | |
|---|---|---|---|
| 8,855,811 B1* | 10/2014 | Schultz .................. | G16H 20/13 700/240 |
| 2022/0055833 A1* | 2/2022 | Lewis .................... | A61J 7/0084 |
| 2022/0115105 A1* | 4/2022 | Nieten ................... | G16H 40/20 |

* cited by examiner

*Primary Examiner* — Gene O Crawford
*Assistant Examiner* — Lester Rushin, III
(74) *Attorney, Agent, or Firm* — K&L Gates LLP

(57) ABSTRACT

A system, method, and apparatus for the routing of totes and bottles within a pharmacy fulfillment center are disclosed. The system, method, and apparatus are configured to transmit routing tables from an application server to station controllers (e.g., PLCs) to enable each station to locally make a routing decision. Since the routing logic is locally stored at each station, the controllers do not need to transmit request messages to the server every time a tote or bottle is scanned. The system, method, and apparatus increase conveyor throughput by enabling each station to make a routing decision without having to wait for a response from a server.

20 Claims, 5 Drawing Sheets

ROUTING OF TOTES AND BOTTLES WITHIN A PHARMACY CONVEYOR SYSTEM

PRIORITY CLAIM

This application claims priority to and the benefit of U.S. Provisional Patent Application Ser. No. 63/164,831, filed on Mar. 23, 2021, the entire disclosure of which is hereby incorporated by reference.

BACKGROUND

Typical pharmacy conveyance systems are configured to process hundreds to thousands of prescriptions a day. These pharmacy conveyance systems may be used for online fulfillment of medication prescriptions where patient-specific local pharmacy preparation is not needed. Some pharmacy systems may use conveyance systems to at least help automate operations that may instead be performed a local pharmacies, such as prescription filling and packaging.

These known pharmacy conveyance systems route totes and bottles along one or more conveyor belts to one or more stations for processing. The stations can be configured for filling a prescription, collating, and/or packing. Some stations may be automatic such that robotic systems automatically perform a programmed operation, such as dispensing medication to a container for prescription filling. Other stations may be manual or semi-automatic where at least some human intervention is needed to complete the filling or packing tasks.

Known pharmacy conveyance systems use pushers to push bottles from a conveyor belt to a station. Additionally, known pharmacy conveyance systems use routers to divert totes to a specific station. The pushers and routers are controlled by a controller, such as a programmable logic controller ("PLC"). These known controllers communicate with a server to determine how totes and bottles are to be routed. The server includes one or more routing tables that are populated with destination station(s) for each tote and/or bottle.

During normal operation, a scanner at a station reads an identifier printed on a barcode that is located on a tote or bottle. The PLC at the station then transmits a request to the server with the identifier. The server looks up the identifier of the tote or bottle in the one or more routing tables to determine a code of a destination station. The server then responds to the PLC with a message containing the code of the destination station. If the code of the destination station does not match a code assigned to a station of the PLC, the PLC permits the tote or bottle to pass to the next station (and corresponding PLC). However, if the code of the destination station matches the code assigned to the PLC station, the PLC causes the pusher/router to move the tote/bottle from the conveyor belt to the station.

The known pharmacy conveyance systems maintain routing tables at the server to provide centralized management of tote and bottle routing. This enables changes to be made to tote and bottle routing without affecting operation of the PLCs at each station of the conveyor belt. This also enables totes and bottles to be added to the tables when entered into a pharmacy system and removed when packing is complete or the tote/bottle reaches its destination.

However, a drawback of known pharmacy conveyance systems is the limitation on conveyor throughput since routing decisions are made centrally at the server. It may take as long as one to three seconds for the server to respond to a PLC request message. During this time, the PLC may be delaying the conveyor belt and/or causing a backup of totes and/or bottles. Further, if a route or destination code is not provided in the routing tables, the PLC may issue an alert or require user intervention. In some instances, totes or bottles with unspecified routes or destinations may loop through the conveyor belt until a destination becomes defined or a manual station becomes active or available, thereby increasing tote/bottle traffic and reducing throughput.

SUMMARY

Example systems, methods, and apparatus are disclosed herein for the routing of totes and bottles within a pharmacy conveyor system. The example systems, methods, and apparatus are configured to transmit routing tables from an application server to station controllers (e.g., PLCs) to enable each station to locally make a routing decision. Since the routing logic is locally stored at each station, the controllers do not need to transmit request messages to the server every time a tote or bottle is scanned. The disclosed systems, methods, and apparatus increase conveyor throughput by enabling each station to make a routing decision without having to wait for a response from a server. In some instances, throughput may be increased up to three seconds per tote or bottle. Further, since tote and bottle routing tables are stored locally at memories or registers of station controllers, each station can determine when to enable a tote or bottle to loop through the conveyor belt if a destination station has not yet been specified, thereby preventing backups at some stations that would otherwise require human intervention.

Each station controller includes, for example, a PLC table interface that is communicatively coupled to an interface at the server. The connectivity between the interfaces enables locally stored routing tables to be updated or replaced remotely by a server without affecting operation of the station controllers. The server may transmit updates for tote/bottle routing tables to a station controller before the tote/bottle reaches the station. For instance, after a bottle passes by one station, the server transmits a bottle routing table to a next station with the appropriate routing information to enable just-in-time decisions.

In other embodiments, the server may transmit updates for bottle routing tables when (e.g., at predefined schedules) new bottles are introduced or programmed into to the pharmacy conveyor system. The server may transmit updates for tote routing tables when totes are reallocated after use. In some instances, the station controllers are configured to transmit alert messages to the server when an identifier of a tote or a bottle is not included within a routing table. At the same time, the station controllers may cause the tote or bottle to be routed to a manual station, if available, or cause the tote or bottle to continue looping around the conveyor belt until updated routing tables are provided with a specified destination.

In light of the disclosure herein and without limiting the disclosure in any way, in a first aspect of the present disclosure, which may be combined with any other aspect listed herein unless specified otherwise, a pharmacy conveyor system includes a pharmacy conveyor belt including a plurality of stations. The conveyor belt for each station includes a reader configured to read a barcode on a tote or a bottle, a pusher configured push the tote from the conveyor belt to the station or a router configured to divert the bottle from the conveyor belt to the station, a controller configured to determine whether the pusher or the router is to be activated based on the read barcode, and a memory device storing a data structure of tote lookup tables and bottle lookup tables. Each tote lookup table includes a tag name corresponding to a respective tote identifier of a tote, and a route code indicative of a current location or an assigned destination of the corresponding tote. Each bottle lookup table includes a bottle identifier, and an assigned destination of the bottle. The pharmacy conveyor system also includes an application server communicatively coupled to the memory device or the controller. The application server is configured to receive prescriptions for filling through a pharmacy workflow, assign the prescriptions to at least one of totes or bottles, and determine routing information for each of the totes and bottles. For the routing information associated with totes, the application server is configured to, for each tote, select a tote lookup table of available totes and update the route code with a destination identifier specified in the respective routing information. For the routing information associated with bottles, the application server is configured to, for each bottle, create a bottle element or entry within a bottle lookup table and create a route code with a destination identifier specified in the respective routing information. The application server is further configured to transmit the tote lookup tables and the bottle lookup tables to the controllers of each station before the respective totes and bottles are received on the conveyor belt.

In a another aspect of the present disclosure, any of the structure, functionality, and alternatives disclosed in connection with any one or more of FIGS. 1 to 7 may be combined with any other structure, functionality, and alternatives disclosed in connection with any other one or more of FIGS. 1 to 7.

In light of the present disclosure and the above aspects, it is therefore an advantage of the present disclosure to provide a pharmacy conveyor system in which routing tables for totes and bottles are transmitted to station controllers to enable routing decisions to be made locally instead of at a server.

It is another advantage of the present disclosure to provide a pharmacy conveyor system with station-based routing decisions to improve throughput and reduce conveyor belt congestion or queues.

It is a further advantage of the present disclosure to provide logic for pharmacy conveyor system controllers that causes bottles or totes with unspecified destinations to be routed to manual stations or continue cycling on a conveyor belt until a destination station is specified.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
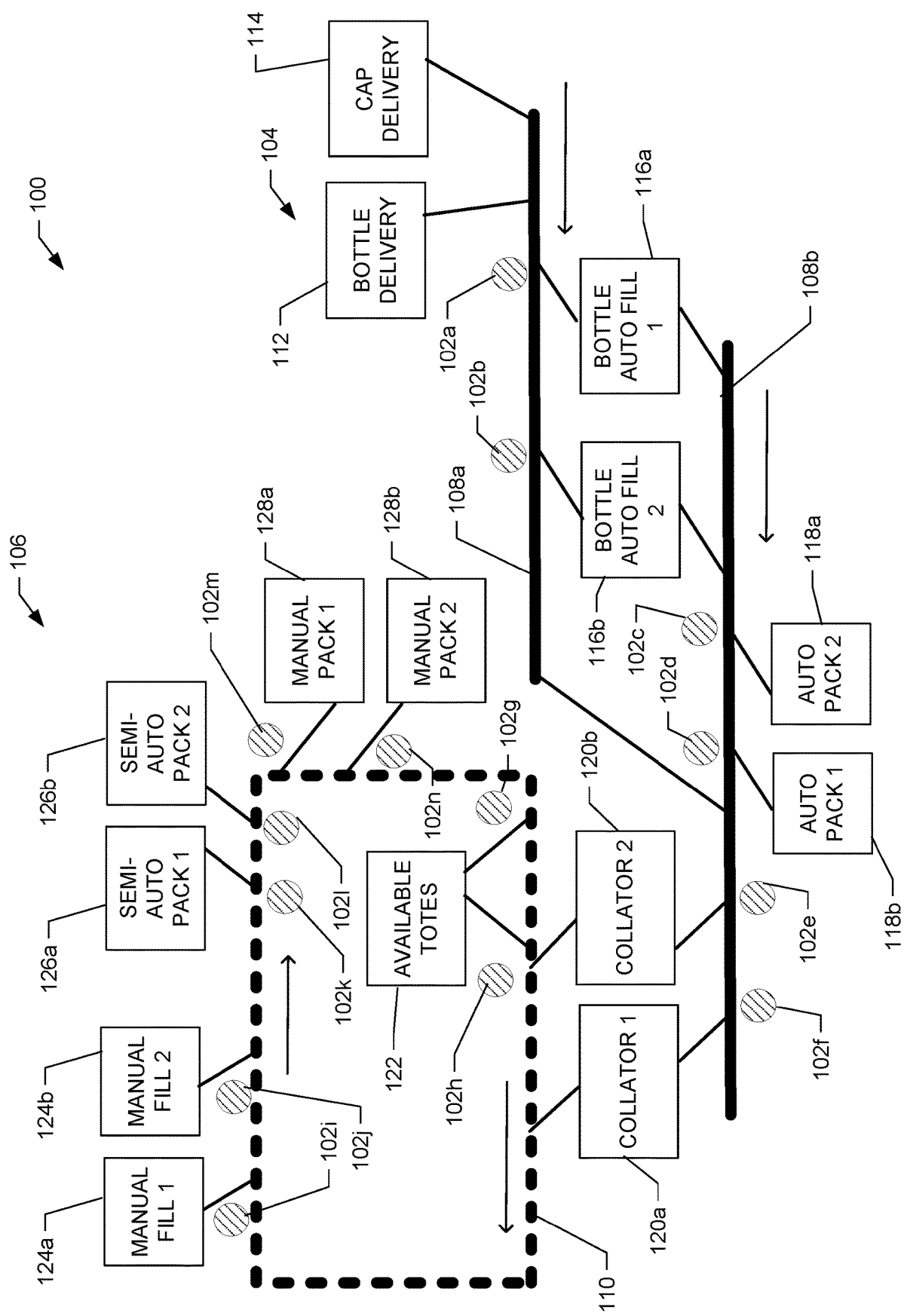
FIG. 1 is a diagram of a pharmacy conveyor system including stations, according to an example embodiment of the present disclosure.

Methods, systems, and apparatus are disclosed herein for a pharmacy conveyor system that enables individual station controllers to perform bottle and tote routing using locally stored routing tables. The example methods, systems, and apparatus are configured to push or otherwise transmit routing tables periodically to routing station controllers located along a conveyor belt. The station controllers use the local routing tables to determine how totes and/or bottles are to be routed without having to query the server. The use of local routing tables at the station controllers improves pharmacy conveyor system throughput by enabling routing decisions to be made instantly instead of having to wait for a response from the server.

In some embodiments, the example server is configured to track locations of totes and/or bottles using assigned identifiers. The identifiers are also printed or otherwise encoded on each respective tote and bottle. Station controllers read an identifier of a tote or bottle, which is then transmitted to the server. The server uses the present location of the tote or bottle to determine one or more next stations that the tote or bottle will pass along the conveyor belt. The server transmits at least a routing table for the tote or bottle to the one or more identified station controllers to enable local just-in-time routing decisions to be made before the tote or bottle arrives at the one or more stations.

In other embodiments, the server is configured to transmit tote and bottle routing tables after totes are reassigned and/or bottles enter into the pharmacy conveyor system. In these examples, the server may transmit periodic updates to station controllers. For example, the server may transmit updated routing tables at periodic times (e.g., every five minutes) or after a batch of changes to the tables are made.

As disclosed herein, each station includes a controller that actuates a pusher or router to move a tote or bottle from a conveyor belt. The disclosed controller includes an interface for receiving routing tables and updates to routing tables. In instances where the controllers include PLCs, the interface may include a PLC table interface. A server is configured to access the controller interface for updating the routing tables.

Reference is made herein to totes and bottles. As disclosed herein, a tote is a bin, puck, vial carrier, or other container for carrying medication packaging or other article on a conveyor belt. A tote may be used when the medication packaging cannot be effectively moved along a conveyor by itself. A tote may also be used to carry medication packaging contents together for final packing at a separate station. A tote includes a unique identifier for tracking the respective tote.

A bottle refers to a medication bottle, vial carrier, or other container for housing or moving medication. A bottle may include a cylindrical container or a package for housing pills or pill packs. A bottle usually includes a lid that is secured during a filling or packing process. A bottle also usually includes a label with prescription and/or medication information. The label may also include a unique identifier for tracking the bottle. In some embodiments, the bottle may include a separate identifier to enable tracking of the bottle itself separate from a medication or prescription assigned to the bottle.

While the example methods, apparatus, and systems are disclosed herein as operating with totes and bottles, it should be appreciated that the methods, apparatus, and systems may be operable with other articles. For example, the methods, apparatus, and systems may provide for the routing of packages in a facility, products to be packaged in a facility, and/or components to be assembled into a product along an assembly line. The methods, apparatus, and systems may also provide for the routing of articles in a pneumatic conveyance system.

Reference is also made herein to prescriptions and medications. A prescription is generated by a pharmacy based on a document (commonly referred to a medication order), which is provided by a clinician. A medication order designates a particular patient for receiving a specified dosage of a medication. References to a prescription herein refer to information from a medication order in addition to prescription fill information for a particular patient/medication. In other words, a prescription is a single medication fill event for a particular patient that is performed by a pharmacy, such as a pharmacy fulfillment center. A medication includes a pill, tablet, or other solid pharmaceutical drug dosage that is consumed by a patient. A medication may also include a compounded pharmaceutical that is prepared from two or more substances. While reference is made to pills/tablets, it should be appreciated that the system disclosed herein may be used for the preparation of any medication type.

Reference is further made herein to (digital) prescription fill information. This information includes a patient identifier, a medication identifier, a medication quantity identifier, a dosage identifier, an urgency identifier, a weight value, a medication shape identifier, a medication manufacturer indicator, a dosage form indicator, a color indicator, a marking indicator, a Drug Enforcement Administration ("DEA") code, an expiration date, medication directions, and/or at least one image of the prescription fill/preparation process.

Pharmacy Conveyor System Embodiment

FIG. 1 is a diagram of a pharmacy conveyor system 100 including stations 102, according to an example embodiment of the present disclosure. The pharmacy conveyor system 100 includes a bottle area 104 and a tote area 106. The bottle area 104 includes a bottle conveyor belt 108 and the tote area 106 includes a tote conveyor belt 110. The bottle conveyor belt 108 is separated into two sections including a fill section 108a and a pack section 108b. The conveyor belt 108 is shown as a loop. It should be appreciated that in different embodiments, the belts 108 and 110 may be provided in alternative arrangements. For example, the bottle conveyor belt 108 may include a loop or a u-shape. Further, the number and placement of the stations 102 may be changed.

In the illustrated embodiment, empty bottles are added to a bottle delivery area 112 and new caps are added to a cap delivery area 114 (e.g., medication fulfillment areas). The bottle delivery area 112 is configured to serially provide medication bottles for filling. The cap delivery area 114 is configured to serially provide caps to close bottles after filling. In some embodiments, the bottles may already have printed labels attached prior to being placed in the bottle delivery area 112. Alternatively, the bottle delivery area 112 may provide for printing labels to bottles. In yet another alternative embodiment, a bottle labeling printing station may be part of the fill section 108a or pack areas discussed below.

As shown in FIG. 1, the fill section 108a includes bottle auto fill machines 116a and 116b (e.g., medication fulfillment areas). Each machine 116 is configured to read an identifier on a bottle label, determine a medication, and cause corresponding pills or tablets to be added to the bottle. The machines 116 are also configured to secure a cap to the bottle after filling. Bottes that cannot be filled automatically maybe routed to manual filling areas, discussed below.

After filling, the machines 116 place the bottles on the conveyor belt of the pack section 108b. Here, the filled bottles may be routed to auto packing machines 118a and 118b. These machines 118a and 118b may automatically place a bottle into a container or box for shipping. Bottles that cannot be filled automatically may be routed to manual or semi-manual packing areas, discussed below.

The example pharmacy conveyor system 100 includes collators 120a and 120b (e.g., medication fulfillment areas) to receive unpacked bottles. The example collators 120a and 120b are configured to accumulate bottles for placement into individual totes. When an available tote is received, the collator 120 places a bottle into the tote. The collators 120 may also receive medication bottles, medication boxes, or other containers that did not originate in the bottle area 104. For example, operators may manually load bottles or other medication containers into the collators 120.

The example tote area 106 includes a rack or structure 122 for managing available totes. The rack 122 may, for example, receive totes after they have been emptied for placement into a queue. When an available tote is needed, the rack 122 is configured to provide a tote to the tote conveyor belt 110. The stations 102g and 102h may scan totes as they enter and leave the rack or structure 122. The tote identifiers recorded during the scan may be sent to an application server 202 (discussed below) to track which totes are located in the rack or structure 122 and available. The rack or structure 122 may be configured in a first-in first-out or a last-in first-out configuration for deploying available empty totes back to the conveyor belt 110.

The tote area 106 also includes manual fill areas 124a and 124b (e.g., medication fulfillment areas). In stances where a prescription cannot be filled using the auto filling machines 116, totes/bottes are routed to the manual fill areas 124. In these areas 124 operators may manually fill a prescription. This can include dispensing pills into a bottle, placing pill packs into boxes, and/or preparing medication compounds. Totes may be routed to manual fill areas 124, then returned to the tote conveyor belt 110 after filling.

The tote area 106 further includes semi-automatic pack areas 126a and 126b and manual pack areas 128a and 128b (e.g., medication fulfillment areas). The semi-automatic pack areas 126 are configured to provide automated assistance for packing bottles or other medication containers. The semi-automatic pack areas 126 may provide for automatic label printing/placement, after which an operator manually packs the medication packaging into containers used for transport/shipping. The manual pack areas 128 may provide for manual label placement and/or manual operator packing into containers used for transport/shipping. After packaging, the bottles are transported to a specified destination, such as a local pharmacy or a patient's residence. Further, after packaging, the totes are returned to the rack 122 via the tote conveyor belt 110.

As mentioned above, the pharmacy conveyor system 100 of FIG. 1 includes pushing/routing stations 102*a* to 102*n*. Each station 102 includes a reader for optically and/or electronically reading a code printed on or otherwise integrated with a tote or a bottle. Each station 102 also includes a pusher or router. Stations 102 that handle bottles may include pushers, which include actuators configured to move a bottle from the conveyor belt 108*a* or 108*b* to a respective machine 116 or 118 or collator 120. Stations that handle totes may include routers configured to divert a tote from the tote conveyor belt 110 to a diversion belt for the rack 122, the fill area 124, or the pack areas 126 and 128. Each station 102 further includes a controller configured to control actuation of the pusher or router based on information received from the reader.

In an example, the station 102*a* is configured to either push bottles to the bottle auto fill machine 116*a* or permit the bottles to pass along the fill section of the bottle conveyor belt 108*a*. In another example, the station 102*i* is configured to either push totes (with bottles or other medication packaging) to the manual fill area 124*a* or permit the totes to pass along the tote conveyor belt 110. In yet another example, the station 102*m* is configured to either push totes (with bottles or other medication packaging) to the manual pack area 128*a* or permit the totes to pass along the tote conveyor belt 110.

Figure 2:
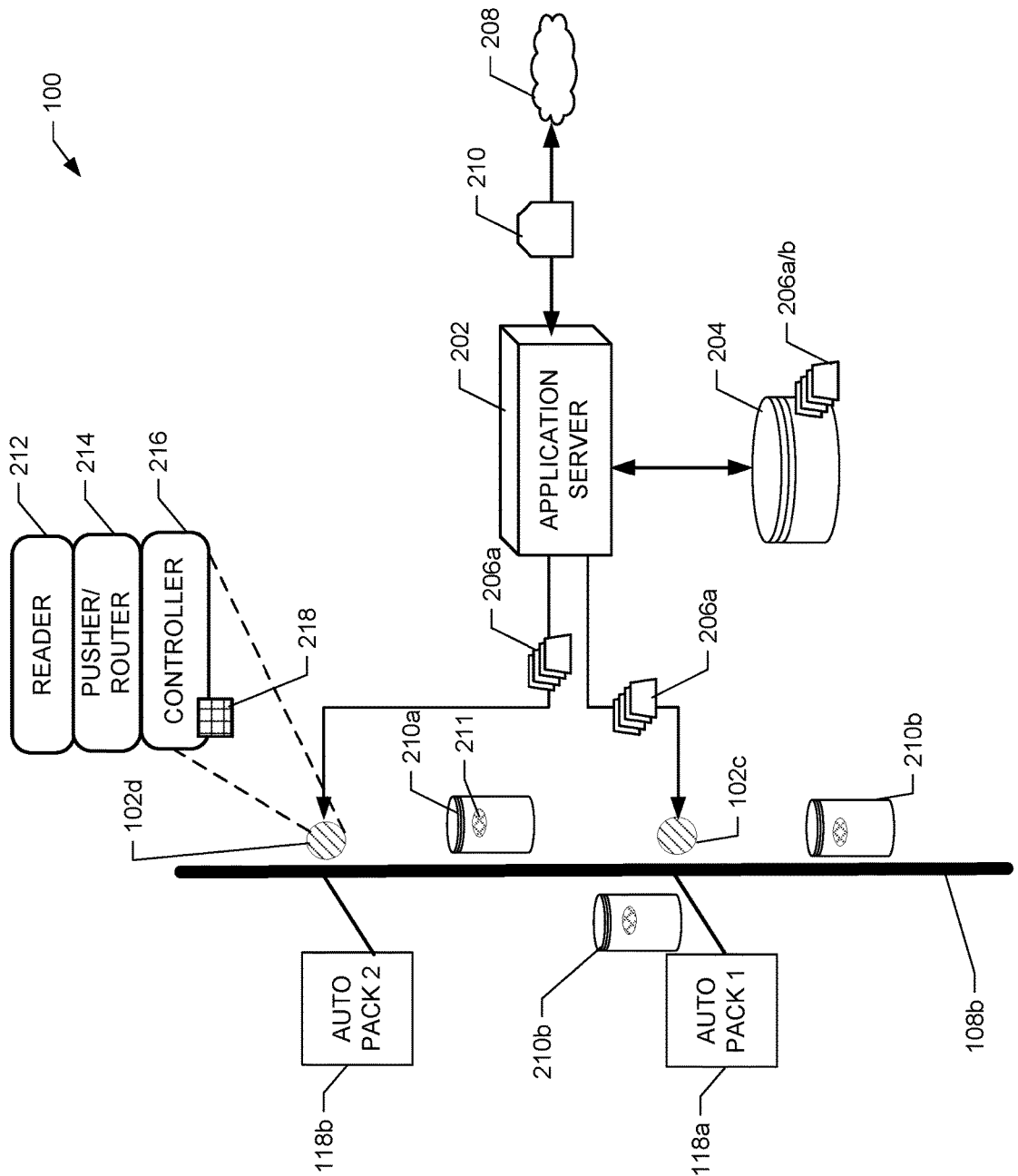
FIG. 2 is a diagram of the pharmacy conveyor system of FIG. 1 including an application server in communication with stations, according to an example embodiment of the present disclosure.

FIG. 2 shows a diagram of the pharmacy conveyor system 100 of FIG. 1 with an application server 202 communicatively coupled to the stations 102, according to an example embodiment of the present disclosure. The application server 202 may be connected to the stations 102*a* to 102*n* via a local area network ("LAN"), a wireless LAN, a serial connection such as RS-232 or RS 485, or a controller area network ("CAN") connection. In some embodiments, the application server 202 may communicate with the stations 102 using a Fieldbus or Hart communication protocol.

The example application server 202 may include a processor, a workstation, a logic controller, a laptop computer, a distributed computing system, etc. The application server 202 may include a memory that stores machine-readable instructions, which when executed by a processor at the server 202, cause the server 202 to perform the operations disclosed herein. Additionally, the application server 202 is communicatively coupled to a memory device 204, which may include any random access memory ("RAM"), read only memory ("ROM"), flash memory, magnetic or optical disks, optical memory, or other storage media. The memory device 204 is configured to store tote and bottle routing tables 206. In some embodiments, the memory device 204 may store the tote and bottle routing tables 206 in a database. In these embodiments, the application server 202 is provisioned as an interface between the stations 102 and the database in the memory device 204.

In the illustrated embodiment, the application server 202 may be communicatively coupled to a pharmacy computer system 208 via a LAN or a wide area network, such as the Internet. The pharmacy computer system 208 is configured to transmit electronic prescription records 210 to the application server 202. Each record 210 specifies patient information and/or medication fill information.

The application server 202 is configured to process the electronic prescription records 210 in a defined workflow to ensure the prescription is fulfilled using the pharmacy conveyor system 100. Processing includes the server 202 determining how the prescription is to be filled, including a bottle type and/or whether the prescription is to be manually filled, auto filled, manually packed, or auto packed. The server 202 determines a route (or a destination station 102) along the conveyor belts 108 and 110 for the prescription. The server 202 further may determine an identifier for a bottle and/or tote for the prescription. The server 202 stores the determined route (or destination station 102) and/or the bottle/tote identifier to a routing record or entry for the tables 206 for a newly received electronic prescription record 210. In some instances, the route specifies one or more stations 102 to which a tote or bottle is to be routed during a fulfillment process. For example, referring to FIG. 1, a route may specify the bottle auto fill area 116*a* and the auto pack area 118*a* associated with the stations 102*a* and 102*d* for routing a bottle. Specifying the bottle auto fill area 116*a* and the auto pack area 118*a* (or identifiers of the respective stations 102*a* and 102*d*) in a routing table 206 for a bottle causes the corresponding pushers at the stations 102*a* and 102*d* to push the bottle to the respective bottle auto fill area 116*a* and the auto pack area 118*a*.

Figure 3:
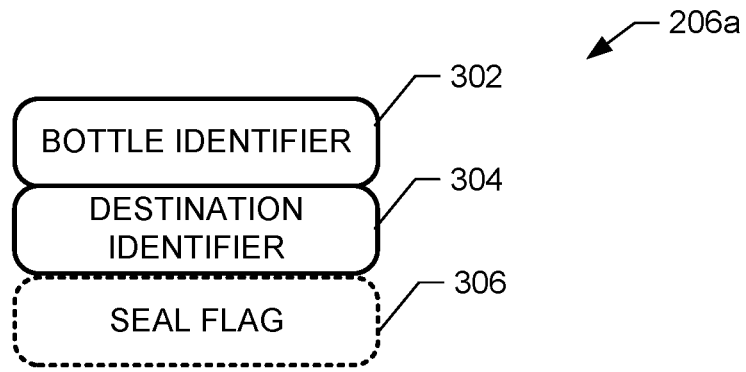
FIG. 3 is a diagram of a bottle routing table, according to an example embodiment of the present disclosure.
Figure 4:
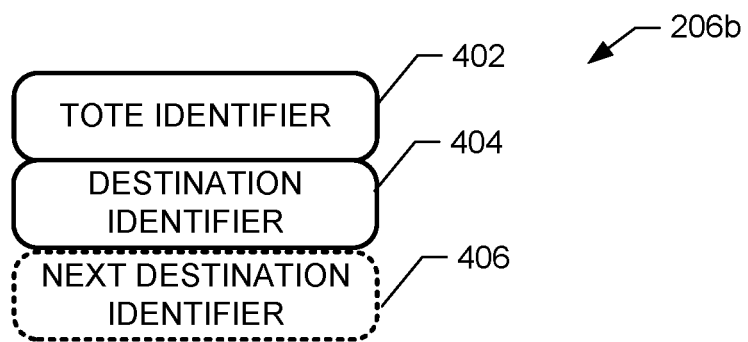
FIG. 4 is a diagram of a tote routing table, according to an example embodiment of the present disclosure.

FIG. 3 is a diagram of an example bottle routing table 206*a* and FIG. 4 is a diagram of an example tote routing table 206*b*, according to example embodiments of the present disclosure. The routing tables 206*a* and 206*b* are created by the application server 202 using electronic prescription records 210. At startup of the system 100, the routing tables 206*a* and 206*b* may be empty. The example bottle routing table 206*a* may include an array of a certain number of elements, such as 10,000 elements. Each element in the table 206*a* is indexed (via a bottle identifier field 302) to a given container identifier of a bottle. The unique identifier may include a 10-digit integer that is printed to a label affixed to the bottle, encoded on a radio-frequency ("RF") tag placed on a bottle, or embedded or integrally formed into a side or bottom of the bottle. The 10-digit number may include a container identifier, which represents an index point for that container within the routing table 206*a*. The use of the container identifier as an index point removes the need for a controller 216 to search the table 206*a* for the bottle identifier 302.

Each element of the table 206*a* may also include a destination field 304 and/or a seal flag/indicator 306. The destination field 304 may include a three, four, five, etc. digit identifier or code. The destination codes may identify a particular auto fill machine 116, a manual fill area 124, a collator 120, an auto pack machine 118, a semi-automatic pack area 126, a manual pack area 128, a bottle collection area 112, an exceptions area, etc. In alternative embodiments, the destination field 304 specifies the station 102*a* to 102*n* that is associated with one of the areas 112, 116, 118, 120, 124, 126, and 128. An inclusion of a destination code within the destination identifier 304 of the table 206*a* specifies a destination to where a bottle is to be routed. The seal flag 306 provides an indication as to whether a bottle should be sealed. In some embodiments, the seal flag 306 may be omitted.

The example application server 202 is configured to determine if an electronic prescription record 210 is indicative that a medication is to be provided via a bottle. If the medication is to be provided via a bottle, the application server 202 generates a unique identifier. The application 202 sever creates an entry or element for the unique identifier. The application server 202 also determines a route or destination for the bottle based on a type of the medication to be dispensed. Some medications types are specified to be dispensed via a machine 116 while other medication types are specified to be filled manually. Further, some medication types are specified to be automatically packed via a machine 118 while other medication types are specified to be filled manually.

The application server 202 is also configured with one or more load balancing algorithms for predicting or estimating loads at each station. For example, after determining that a medication is specified for automated filling, the application server 202 may select between one of the autofill machines 116a and 116b. The selection may be periodic where the application server 202 alternates between assigning the machines 116a and 116b. In other embodiments, the application server 202 may receive status information, such as a percent capacity from each station (or whether the station is available), which is used for assigning a route or destination. After determining a destination or route, the application server 202 assigns a code or identifier of the destination or route to the destination field 304 of the bottle routing table 206a.

As empty totes are added to the system 100, the totes are assigned an identifier or code. The identifier or code is static for the tote and does not change for different medication fulfillments. The tote routing table 206b of FIG. 4 may include an array of a certain number of elements, such as 10,000 elements. Each element in the table 206b is indexed (via a tote identifier field 402) to a unique identifier or code for a respective tote. The unique identifier or code is also printed on a label that is affixed to the respective tote or encoded in an RF tag placed on the tote. The tote identifier field 402 may include a 10-digit number that comprises a container identifier, which represents an index point for that container within the routing table 206b. The use of the container identifier as an index point removes the need for a controller 216 to search the table 206b for the tote identifier 402.

As shown in FIG. 4, each element includes a destination identifier 404 (e.g., a route code). Further, each element of the table 206b may include a next destination identifier 406 (e.g. a next route code). The destination identifier 404 specifies a current location and/or an in transit destination for the tote. The next destination identifier 406 specifies a next destination for a tote.

As disclosed herein, each station 102 is assigned a unique destination code, which may include a three, four, five, etc. digit identifier or code. The destination codes may be the same as the destination codes for the bottles. An inclusion of a destination code within the destination identifier 404 of the table 206b specifies a destination to where a tote is to be routed. The application server 202 is configured to determine a route or a destination for each tote in a similar manner as the bottles discussed above. For instance, the route or destination may be determined based on a medication type to be filled and/or a capacity/availability of stations 102.

Returning to FIG. 2, the diagram shows the application server 202 in communication with a first station 102c for a first auto pack machine 118a and a second station 102d for a second auto pack machine 118b. The application server 202 is configured to transmit the bottle routing tables 206a to the stations 102c and 102d after routes for bottles are defined. In some embodiments, the application server 202 is configured to transmit the bottle routing tables 206a after the routes are determined. In other instances, the application server 202 is configured to transmit the bottle routing tables 206a while a bottle is in transit. For example, the application server 202 detects that a bottle 210a has just passed the station 102c (e.g., the station 201c transmits a message indicative that an identifier corresponding to the bottle 210a has just been scanned). The application server 202 may also determine that the bottle 210a is assigned a destination route corresponding to the station 102d. The application server 202 accordingly transmits an updated bottle routing table 206a with a route for the bottle 210a to the station 102d. In this example, the station 102d receives the updated bottle routing table 206a and determines that the bottle is to be pushed to the second auto pack machine 118b.

In some embodiments, the application server 202 is configured to change a destination of a bottle or a tote after the bottle or the tote has reached a first destination. For example, after reaching an assigned fill machine or area, the application server 202 determines a pack machine or area. The application server 202 accordingly transmits an updated routing table 206 to enable packing of the medication after filling. In this example, the application server 202 receives an indication from a destination station 102 that a tote or bottle has arrived. In response, the application server 202 is configured to determine a next destination station 102 for packing or other intermediate handling.

As shown in FIG. 2, each station 102 includes a reader 212, an actuator 214, and a controller 216. The example reader 212 may include any optical, RF, acoustic, etc. device that is configured to emit light, RF signals, acoustic waves, etc. and detect a response from an object. The reader 212 is configured to read an identifier 211 on a tote or bottle. In some embodiments, the reader 212 may be positioned below a conveyor belt 108 or 110 for reading a bottom of the tote or bottle. Alternatively, when the identifier 211 is placed on a side of the tote or bottle 210, the reader 212 may be positioned on a side of the conveyor belt 108 or 110.

Figure 5:
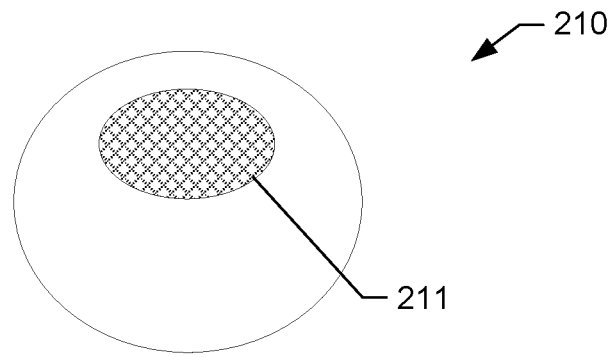
FIG. 5 is a diagram of a bottle with an identifier placed on a bottom of the bottle, according to an example embodiment of the present disclosure.

FIG. 5 is a diagram of a bottle 210 with an identifier 211 placed on a bottom side, according to an example embodiment of the present disclosure. The identifier 211 may be integrally formed with the bottle 210 and/or placed on a printed label that is affixed to a bottom of the bottle 210. The identifier 211 may include a line bar code or a two-dimensional bar code. The placement of the identifier 211 on the bottom of the bottle 210 may enable the identifier 211 to be identified on a first read attempt without having to turn or otherwise manipulate the bottle 210. Placement of the identifier 211 on a side of the bottle 210 in contrast may require the bottle 210 to be turned on the conveyor belt 108/110 to provide alignment with the reader 212.

Returning to FIG. 2, the actuator 214 of the station 102 is configured to move a bottle or tote from the conveyor belt 108/110 to a machine or pack/fill area. For bottle-related conveyor belts 108, the actuator 214 may include a bottle pusher. For tote-related conveyor belts 110, the actuator 214 may include a router to divert totes.

The actuator 214 is controlled by the controller 216 of the respective station 102. The example controller 216 may include a PLC or other logic controller configured to determine how totes and/or bottles are to be routed based on one or more bottle or routing tables 206. The controller 216 includes an interface 218 that is communicatively coupled to the application server 202 via a network or serial connection. The interface 218 is configured to receive the tote or bottle routing tables 206 from the application server 202. Upon receipt, the controller 216 is configured to store the tote and/or bottle routing tables 206 to a local memory. The interface 218 is configured to permit the application server 202 to make updates or overwrite routing tables 206.

In the illustrated example of FIG. 2, the interface 218 receives a bottle routing table 206a from the application server 202. The controller 216 stores the bottle routing table 206a to a local memory. Later, the reader 212 scans the identifier 211 on the bottle 210a when the bottle 210a reaches the station 102d via the conveyor belt 108b. The controller 216 identifies the bottle identifier from the scan information encoded in the identifier 211. The controller 216 compares the bottle identifier to indexed bottle identifiers in the bottle routing table 206a. If there is a match, the controller 216 identifies the destination identifier from the corresponding destination field 304. The controller 216 compares the destination identifier from the field 304 to the assigned code or identifier of the station 102d, which may be stored to a memory register of the controller 216. If the identifiers match, the controller 216 causes the actuator 214 to push the bottle 210a to the auto pack machine 118b. If the identifiers do not match, the controller 216 permits the bottle 210a to pass by along the conveyor belt 108b. As shown in FIG. 2, the controller 216 of the station 102c has determined that the bottle 210b is to be pushed to the auto pack machine 218a.

In the example of FIG. 2, the controller 216 may also transmit a notification or ping message to the application server 202. The controller 216 transmits the notification or ping message after scanning a bottle 210. The message includes an identifier 211 of the bottle 210 and/or an identifier of the station 102. The application server 202 uses information in the message to determine that the bottle 210 is currently at the station 102 specified by the identifier.

In some embodiments, the controller 216 may determine that an identifier 211 of a bottle 210 does not match any identifiers in a bottle routing table 206a. In these examples, the controller 216 may request an updated table 206a from the application server 202. Additionally or alternatively, the controller 216 is configured to generate an alarm or alert, which is transmitted to the application server 202 to obtain operator intervention. In some instances, the controller 216 is configured to hold the bottle until a destination is received. In other instances, the controller 216 is configured to enable the bottle to pass by along the conveyor belt 108/110.

It should be appreciated that the application server 202 does not broadcast the same tote and bottle routing tables 206 to all stations 102. For example, the application server 202 may transmit tote routing tables 206b only to the stations 102g to 102n that are specified as handling totes and bottle routing tables 206a only to the stations 102a to 102f that are specified as handling bottles. Further, routing tables 206 with fill destinations are transmitted to the stations 102a, 102b, 124a, and 124b, for example, that are associated with medication filling while routing tables 206 with pack destinations are transmitted to the stations 102c, 102d, 126a, 126b, 128a, and 128b, for example, that are associated with medication packing.

The application server 202 may include a data structure that relates an electronic address of each station 102 with a destination identifier and a corresponding list of operations associated with the respective station. For instance, some stations 102 are associated with packing while some stations 102 are associated with filling. Further, some stations 102 may be associated with bottles while other stations are associated with totes. Alternatively, the destination identifier may be encoded with information that specifies tote/bottle and/or pack/fill responsibilities of the station 102, which is used by the application server 202 to determine which stations 102 are to receive which routing tables 206.

In some instances, the controllers 216 have memory for a limited number of bottles or totes. The memory may be limited by a number of available registers. In these examples, the application server 202 is configured to track the location of each tote and/or bottle on the conveyor belts 108/110. The application server 202 transmits to a station 102 the tote or bottle tables 206 with just routing information for the next one or few totes or bottles to be received. In this manner, the server 202 does not broadcast the tote and routing tables 206 to every station 102, but rather provides routing information for the totes and bottles that are about to be received at a target station. In these instances, the application server 202 uses a current location of a tote or bottle (as determined from messages from controllers 216 at stations 102), to determine a next station. The application server 202 then transmits a routing table 206 for that tote or bottle to the next one or few stations 102 to enable the controllers 216 to make routing decisions.

Manual Pack Station Controller Logic Embodiment

FIG. 1 shows station 102m for the manual pack area 128a and station 102n for the manual pack area 128b. A controller 216 for the station 102m is configured to cause an actuator 214 to divert totes to the manual pack area 128a. Totes that are not diverted to the manual pack area 128a continue on the conveyor belt 110. As totes approach the station 102m, the reader 212 of the station 102m reads the respective tagged identifier on the totes. The controller 216 of the station 102m uses the identifier for comparison to the tote identifier index numbers in the routing table 206b. If tote data is found in the routing table 206b for the station 102m, where the tote identifier matches an index number (e.g., value of a tote identifier field 402), then the controller 216 is configured to use the following logic table conditions to determine whether to use the actuator 214 to divert the tote to the manual pack area 128a.

| Route Code (Destination Route) | Route Code Requested Station (Active, Inactive) | MP1 Gravity Feed Full (On, Off) | Push to Manual Pack Station 1 (Yes, No) |
| --- | --- | --- | --- |
| 5201 | Active | Off | Yes |
| 5200 | Active (Station 5201) | Off | Yes |
| Not applicable | Not applicable | On | No |
| Not applicable | Inactive | Not applicable | No |
| 5202 | Not applicable | Not applicable | No |

In the example, the controller 216 is configured to permit a tote to pass along the conveyor belt 110 (to an exception path) if the destination identifier in the routing table 206b is not one of the listed destination identifiers in the table above. Further, based on the table above, the controller 216 is configured to divert a tote to the manual pack area 128a if an RF tag cannot be read, the manual pack area 128a is available to accept totes, and the manual pack area 128a is not full. However, if the tag cannot be read but the manual pack area 128a is full or inactive, the controller 216 is configured to permit the tote to pass to the next station 102n. Additionally, based on the table above, the controller 216 is configured to divert a tote to the manual pack area 128a if the routing table 206b does not include the tote identifier, the manual pack area 128a is available to accept totes, and the manual pack area 128a is not full. However, if the tote identifier does not match identifiers in the table 206b, but the manual pack area 128a is full or inactive, the controller 216 is configured to permit the tote to pass to the next station 102n. Moreover, the controller 216 is configured to divert a tote to the manual pack area 128a if the tote identifier corresponds to a destination identifier that is less than '5200' or greater than '5202', the manual pack area 128a is available to accept totes, and the manual pack area 128a is not full. However, if the tote identifier corresponds to a destination identifier that is less than '5200' or greater than '5202', but the manual pack area 128a is full or inactive, the controller 216 is configured to permit the tote to pass to the next station 102n. Further, the controller 216 is configured to divert a tote to the manual pack area 128a if the tote identifier corresponds to '5201', the manual pack area 128a is available to accept totes, and the manual pack area 128a is not full.

In the example above, the controller 216 is configured to receive a status from the manual pack area 128a. The status may be indicative as to whether the manual pack area 128a is active and/or whether the manual pack area 128a is full. The status may be transmitted by a switch at the manual pack area 128a or sensed by a queue sensor at the manual pack area 128a.

It should be appreciated that each controller 216 of the stations 102 may include a similar logic table. The use of a logic table at each controller 216 permits routing decisions to be made locally without having to wait for a server to respond. The logic provide routing decisions even when a tote or bottle may not be specified in a routing table or when certain stations go offline or become full. In some embodiments, the logic tables may only provide for routing if a tote or bottle destination matches the identifier of the station 102. If a destination of the tote or bottle does not match the identifier of these stations, the controller 216 is configured to permit the bottle or tote to pass along on the conveyor belt 108/110.

Example Tote and Bottle Routing Table Procedures

Figure 6:
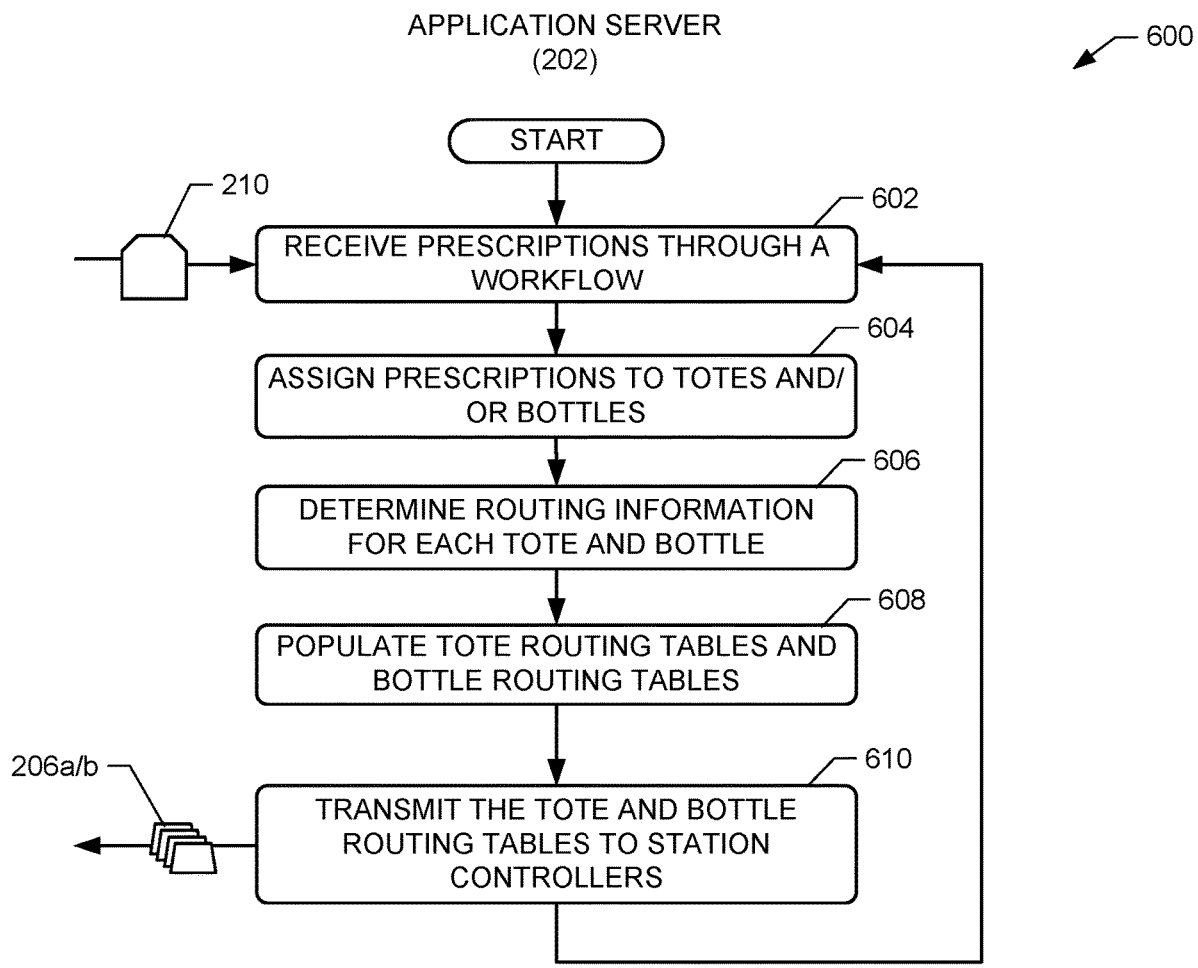
FIG. 6 is a flow diagram of an example procedure for creating tote and/or bottle routing tables, according to an example embodiment of the present disclosure.

FIG. 6 is a flow diagram of an example procedure 600 for creating a tote and/or bottle routing table 206, according to an example embodiment of the present disclosure. Although the procedure 600 is described with reference to the flow diagram illustrated in FIG. 6, it should be appreciated that many other methods of performing the steps associated with the procedure 600 may be used. For example, the order of many of the blocks may be changed, certain blocks may be combined with other blocks, and many of the blocks described may be optional. In an embodiment, the number of blocks may be changed based on a number of factors that account for tote or bottle routing, such as medication type. The actions described in the procedure 600 are specified by one or more instructions and may be performed among multiple devices including, for example the application server 202.

The example procedure 600 begins when the application server 202 receives electronic prescription records 210 from a pharmacy computer system 208 (block 602). The application server 202 then assigns each prescription in the electronic prescription records 210 to a tote and or bottle by generating and assigning a tote and/or bottle identifier (block 604). The application server 202 also determines routing and/or destination information for each tote and/or bottle (block 606). As discussed above in connection with FIG. 2, the application server 202 may use a medication type and/or electronic prescription records 210 to determine whether the medication can be filled in a bottle or via a tote. Further, the application server 202 may use the medication type to determine if the medication can be packaged manually or automatically. The application server 202 is configured to use these specified correlations with medication type to assign a tote/bottle identifier and a route/destination. The application server 202 may determine multiple destinations for each prescription, such as a fill station and a pack station. In some instances, the application server 202 may use a known availability and/or activation of a station 102 when selecting a destination identifier or code.

The example procedure 600 of FIG. 6 continues when the application server 202 populates or writes to a tote or bottle routing table 206 to fill a prescription (block 608). This operation may include writing a destination identifier in a destination identifier field of the appropriate routing table 206b for a particular tote. This operation may include creating a bottle element and writing a destination identifier in a destination identifier field and a bottler identifier in a bottle identifier field of the appropriate routing table 206a. The application server 202 then transmits the tote and/or routing tables 206 to the appropriate stations 102 (block 610). In some embodiments, the application server 202 transmits the routing tables 206 periodically. Alternatively, the application server 202 may track a location of each tote and/or bottle on the conveyor belts 108 and 110 and transmit at least portions of the routing tables 206 to next stations respectively for the totes and bottles. In these instances, the application server 202 receives messages from each station 102 indicative of a tote or bottle identifier read by a reader 212. The application server 202 uses these messages to identify next stations 102 for transmitting the tote and/or bottle routing tables 206. The example procedure 600 then returns to block 602 when additional electronic prescription records 210 are received.

Figure 7:
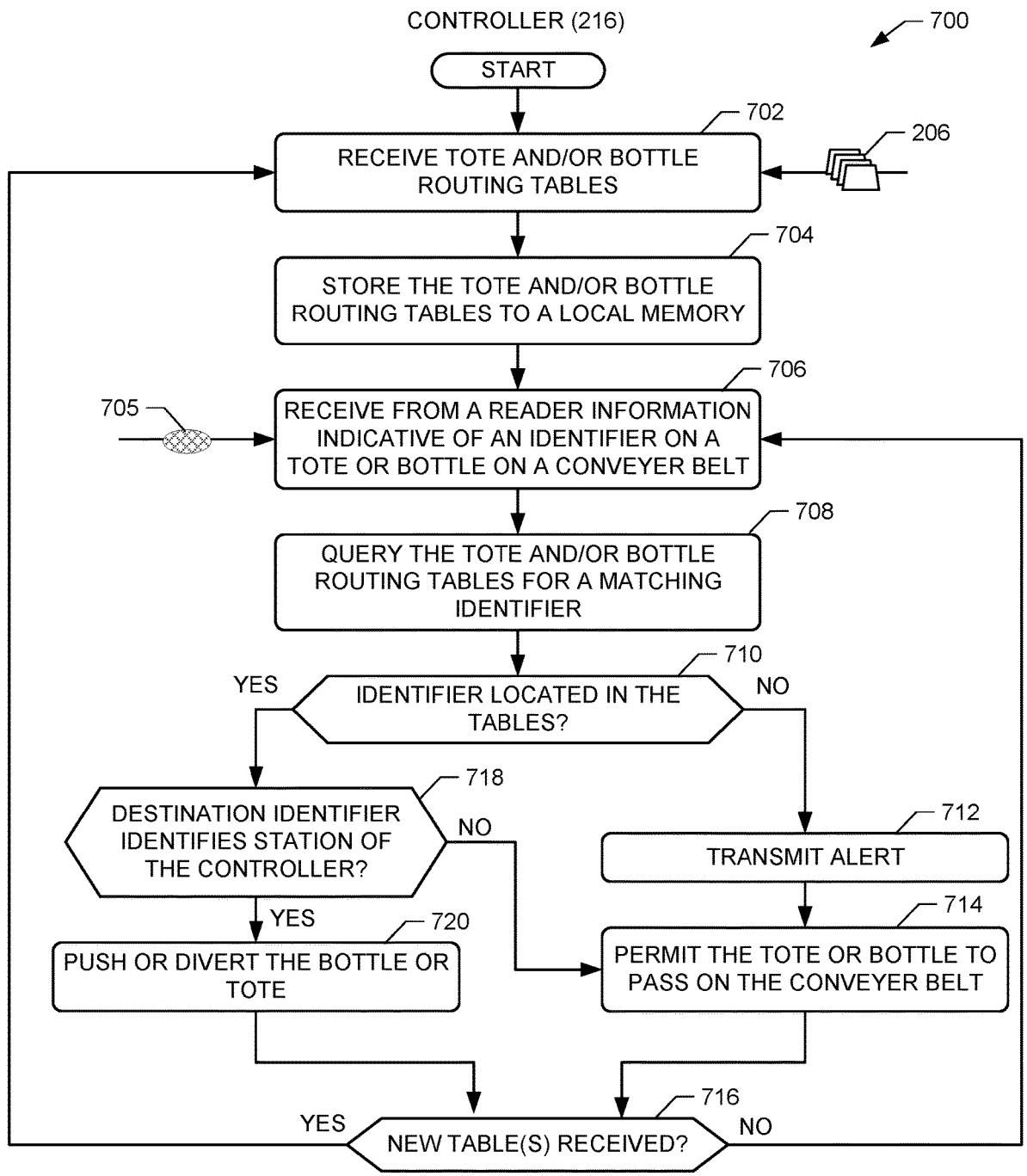
FIG. 7 is a flow diagram of an example procedure for determining whether a tote/bottle is to be pushed/diverted based on a respective tote or bottle routing table, according to an example embodiment of the present disclosure.

FIG. 7 is a flow diagram of an example procedure 700 for determining whether a tote/bottle is to be pushed/diverted based on a respective tote or bottle routing table 206, according to an example embodiment of the present disclosure. Although the procedure 700 is described with reference to the flow diagram illustrated in FIG. 7, it should be appreciated that many other methods of performing the steps associated with the procedure 700 may be used. For example, the order of many of the blocks may be changed, certain blocks may be combined with other blocks, and many of the blocks described may be optional. In an embodiment, the number of blocks may be changed based on programmed logic that addresses routing contingencies. The actions described in the procedure 700 are specified by one or more instructions and may be performed among multiple devices including, for example the controller 216 of each station 102.

The example procedure 700 begins when the controller 216 receives (via the interface 218) a tote and/or bottle routing table 206 from the application server 202 (block 702). The controller 216 may receive the routing table 206 before a respective tote or bottle associated with the table arrives or at periodic intervals. The controller 216 stores the routing table 206 to a local memory (block 704).

The controller 216 at the station 102 then receives information 705 that is read or scanned by a reader 212 (block 706). The information 705 is indicative of a tote or bottle identifier for a tote or bottle on the conveyor belt. In some instances, the controller 216 may transmit a message to the application server 202 indicative of the tote or bottle identifier. The controller 216 uses the tote or bottle identifier from the information 705 to query or search for a matching indexed identifier in the tote or bottle routing table 206 (block 708). The controller 216 determines if there is a match between identifiers (block 710). If there is not a match, the controller 216 may transmit an alert (block 712) to the application server 202 and/or permit the tote or bottle to pass on the conveyor belt 108/110 (block 714). Depending on contingencies specified in a local logic table, the controller 216 in alternative embodiments may push or divert the tote or bottle to a station. The logic of the controller 216 may default to a push or diversion if an identifier cannot be located and/or if the station 102 is a manual station where an operator can perform a manual fill or pack.

After making a decision on a current tote or bottle, the controller 216 determines if another tote or bottle routing table 206 has been received (block 716). If a new table 206 has not been received, the procedure 700 returns to block 706 for the next scanned bottle or tote. However, if a new tote or bottle routing table 206 has been received, the procedure 700 returns to block 702.

Returning to block 710, if there is a match between tote or bottle identifiers, the controller 216 determines if a destination identifier in the table 206 corresponds to a coded identifier of the present station 102 (block 718). If there is not a match, the controller 216 may permit the tote or bottle to pass on the conveyor belt 108/110 (block 714). Depending on contingencies specified in a local logic table, the controller 216 in alternative embodiments may push or divert the tote or bottle to a station. If the present station 102 is specified as the destination of the tote or bottle in the routing table 206, the controller 206 causes an actuator 214 to push or divert the tote or bottle to the corresponding machine or area for processing (block 720). After making a decision on a current tote or bottle, the controller 216 determines if another tote or bottle routing table 206 has been received (block 716). If a new table 206 has not been received, the procedure 700 returns to block 706 for the next scanned bottle or tote. However, if a new tote or bottle routing table 206 has been received, the procedure 700 returns to block 702.

CONCLUSION

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A pharmacy conveyor system comprising:
a memory device configured to store a data structure of at least one tote lookup table and at least one bottle lookup table,
  each tote lookup table including a tag name corresponding to a respective tote identifier of a tote and a route code indicative of a current location or an assigned destination of the corresponding tote, and
  each bottle lookup table including a bottle identifier and an assigned destination of the bottle;
a pharmacy conveyor belt including a plurality of stations, the conveyor belt for each station including:
  a reader configured to read a barcode on a tote or a bottle,
  a pusher configured push the tote from the conveyor belt to a medication fulfillment area or a router configured to divert the bottle from the conveyor belt to a medication fulfillment area, and
  a controller configured to receive at least one of the tote lookup tables or one of the bottle lookup tables and determine whether the pusher or the router is to be activated based on the read barcode matching a tote identifier in the tote lookup table or a bottle identifier in the bottle lookup table; and
an application server communicatively coupled to the memory device, the application server configured to:
  receive prescriptions for filling through a pharmacy workflow,
  assign each of the prescriptions to at least one of a tote or a bottle,
  determine routing information for each of the totes and bottles,
  for the routing information associated with totes, for each tote select a corresponding tote element in one of the tote lookup tables in the memory device and update the route code with a destination identifier specified in the respective routing information,
  for the routing information associated with bottles, for each bottle create a bottle element within one of the bottle lookup tables in the memory device using an assigned bottle identifier and write a route code with a destination identifier specified in the respective routing information,
  transmit the tote lookup tables to the controllers associated with totes before the respective totes are received on the conveyor belt, and
  transmit the bottle lookup tables to the controllers associated with bottles before the respective bottles are received on the conveyor belt.

2. The system of claim 1, wherein the application server includes an interface to the controllers of each station for transmitting at least one of the tote lookup tables or one of the bottle lookup tables.

3. The system of claim 1, wherein the controllers of each station include an interface to the application server for receiving at least one of the tote lookup tables or one of the bottle lookup tables.

4. The system of claim 1, wherein the application server is configured to transmit the tote lookup tables or the bottle lookup tables to the controllers of the stations for which the respective tote is to be pushed or the respective bottle is to be diverted before the tote or bottle has arrived at the respective station.

5. The system of claim 1, wherein the plurality of stations is associated with manual fill areas, auto-fill areas, semi-auto-pack areas, manual pack areas, auto-pack areas, and at least one collator.

6. The system of claim 1, wherein the bottle lookup tables include a seal flag to indicate whether a respective bottle should be sealed.

7. The system of claim 1, wherein the controllers include programmable logic controllers ("PLCs").

8. The system of claim 1, wherein the application server is further configured to:
  receive a message from one of the controllers that a tote has passed through;
  update the tote routing table associated with the tote with a next destination identifier of the routing information; and
  transmit the updated tote routing table to the controller that corresponds to the next destination.

9. The system of claim 1, wherein the controller for each station is further configured to:

receive at least one of the tote lookup tables or one of the bottle lookup tables;
store the at least one of the tote lookup tables or one of the bottle lookup tables to a local memory;
receive from the reader of the same station, information that is indicative of a tote identifier or a bottle identifier;
identify the tote or bottle identifier respectively within the tote lookup tables or the bottle lookup tables;
determine if the specified destination identifier corresponds to an identifier of the controller; and
cause the pusher to push the tote off the conveyor belt or cause the router to divert the bottle from the conveyor belt if the specified destination identifier corresponds to the identifier of the controller.

10. The system of claim 9, wherein the controller for each station is further configured to:
determine the tote or bottle identifier is not located in the respective tote lookup tables or the bottle lookup tables;
cause the tote or bottle to pass through; and
transmit an alert to the application controller indicative of the tote or bottle identifier not being located in the respective tote lookup tables or the bottle lookup tables.

11. The system of claim 1, wherein the totes include a radio frequency ("RF") tag placed on a bottom of the tote, the RF tag including the tote identifier and being readable by the readers of the stations.

12. The system of claim 1, wherein the bottles include a one-dimensional barcode or a two-dimensional barcode including the identifier of the bottle that is printed on a label, the one-dimensional barcode or the two-dimensional barcode being readable by the readers of the stations.

13. The system of claim 1, wherein the bottles include a one-dimensional barcode or a two-dimensional barcode including the identifier of the bottle that is embedded on a bottom of the bottle, the one-dimensional barcode or the two-dimensional barcode being readable by the readers of the stations.

14. A pharmacy conveyor method comprising:
receiving, in an application server, prescriptions for filling through a pharmacy workflow;
assigning, via the application server, each of the prescriptions to at least one of a tote or a bottle;
determining, via the application server, routing information for each of the totes and bottles;
for the routing information associated with totes, for each tote selecting, via the application server, a corresponding tote element in a tote lookup table in a memory device and updating a route code with a destination identifier specified in the respective routing information;
for the routing information associated with bottles, for each bottle creating, via the application server, a bottle element within a bottle lookup table in the memory device using an assigned bottle identifier and writing a route code with a destination identifier specified in the respective routing information;
transmitting, from the application server to controllers associated with totes, the tote lookup table before the respective totes are received on a conveyor belt; and
transmitting, from the application server to controllers associated with bottles, the bottle lookup table before the respective bottles are received on the conveyor belt.

15. The method of claim 14, further comprising before the prescriptions are received in the application server:
creating, via the application server, the tote lookup table by adding a tag name corresponding to a respective tote identifier of a tote, and a route code corresponding to a current location or an assigned destination of the corresponding tote;
creating, via the application server, the bottle lookup table by adding a bottle identifier field and an assigned destination field for a bottle; and
storing the tote lookup table and the bottle lookup table to the memory device.

16. The method of claim 15, further comprising for the controllers associated with totes:
receiving, in the controllers, the tote lookup table;
receiving, via a reader, information from a barcode on a tote, the information including a tote identifier;
determining a destination identifier of the tote by matching, via the controllers, the tote identifier from the barcode to tote identifiers of the tote lookup table;
when the destination identifier matches an identifier of the controller, causing, via the corresponding controller, a pusher to push the tote from the conveyor belt to a corresponding medication fulfillment area; and
when the destination identifier does not match an identifier of the controller, enabling, via the corresponding controller, the tote to pass by along the conveyor belt.

17. The method of claim 16, further comprising for the controllers associated with totes:
determining, via at least one of the controllers, the tote identifier is not located in the tote lookup table;
causing, via the at least one controller, the tote to pass through along the conveyor belt; and
transmitting, from the at least one controller, an alert to the application controller indicative of the tote identifier not being located in the tote lookup table.

18. The method of claim 15, further comprising for the controllers associated with bottles:
receiving, in the controllers, the bottle lookup table;
receiving, via a reader, information from a barcode on a bottle, the information including a bottle identifier;
determining an assigned destination identifier of the bottle by matching, via the controllers, the bottle identifier from the barcode to bottle identifiers of the bottle lookup table;
when the assigned destination identifier matches an identifier of the controller, causing, via the corresponding controller, a router to divert the bottle from the conveyor belt to a corresponding medication fulfillment area; and
when the destination identifier does not match an identifier of the controller, enabling, via the corresponding controller, the bottle to pass by along the conveyor belt.

19. The method of claim 18, further comprising for the controllers associated with bottles:
determining, via at least one of the controllers, the bottle identifier is not located in the bottle lookup table;
causing, via the at least one controller, the bottle to pass through; and
transmitting, from the at least one controller, an alert to the application controller indicative of the bottle identifier not being located in the bottle lookup table.

20. The method of claim 14, further comprising:
receiving, in the application server, a message from one of the controllers that a tote has passed through;
updating, via the application server, the tote routing table associated with the tote with a next destination identifier of the routing information; and transmitting, from the application server, the updated tote routing table to at least the controller that corresponds to the next destination.

\* \* \* \* \*